(12) United States Patent
Ishikawa et al.

(10) Patent No.: US 11,542,367 B2
(45) Date of Patent: Jan. 3, 2023

(54) MEDICAL POLYMER MATERIAL HAVING EXCELLENT BONE-BONDING PROPERTY

(71) Applicant: KYUSHU UNIVERSITY, NATIONAL UNIVERSITY CORPORATION, Fukuoka (JP)

(72) Inventors: Kunio Ishikawa, Fukuoka (JP); Kanji Tsuru, Fukuoka (JP); Akira Tsuchiya, Fukuoka (JP); Yuki Sugiura, Fukuoka (JP); Yasuharu Nakashima, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 594 days.

(21) Appl. No.: 16/613,989

(22) PCT Filed: May 16, 2018

(86) PCT No.: PCT/JP2018/018837
§ 371 (c)(1),
(2) Date: Nov. 15, 2019

(87) PCT Pub. No.: WO2018/212209
PCT Pub. Date: Nov. 22, 2018

(65) Prior Publication Data
US 2020/0354521 A1 Nov. 12, 2020

(30) Foreign Application Priority Data
May 17, 2017 (JP) .............................. JP2017-097776

(51) Int. Cl.
*C08G 65/48* (2006.01)
*A61L 27/18* (2006.01)
(Continued)

(52) U.S. Cl.
CPC .............. *C08G 65/48* (2013.01); *A61L 27/18* (2013.01); *A61L 27/50* (2013.01); *C08G 65/4012* (2013.01); *A61L 2430/02* (2013.01)

(58) Field of Classification Search
CPC ...... A61L 27/18; A61L 27/50; A61L 2430/02; C08L 71/00; C08G 65/48; C08G 65/4012
See application file for complete search history.

(56) References Cited

U.S. PATENT DOCUMENTS 4,795,475 A * 1/1989 Walker ................... A61L 27/14
606/76
6,066,176 A * 5/2000 Oshida ................ A61F 2/30907
623/23.62
10,195,308 B2 2/2019 Murphy et al.
(Continued)

FOREIGN PATENT DOCUMENTS

EP 0212193 A2 3/1987
EP 2380600 A1 10/2011
(Continued)

OTHER PUBLICATIONS

Huang et al. "Phosphorylated poly(sebacoyl diglyceride)—a phosphate functionalized biodegradable polymer for bone tissue engineering" in the Journal of Materials Chemistry B, 2016. (Year: 2016).*

(Continued)

*Primary Examiner* — Blessing M Fubara
(74) *Attorney, Agent, or Firm* — Greenblum & Bernstein, P.L.C.

(57) ABSTRACT

A medical polymer material in which a phosphate group having a C—O—P chemical bond including elemental C in a main chain of a structural formula is present on a surface of a polymer material substantially free of phosphate and hydroxy groups except for ends in the structural formula.

10 Claims, 2 Drawing Sheets

(51) Int. Cl.
*A61L 27/50* (2006.01)
*C08G 65/40* (2006.01)

(56) References Cited

U.S. PATENT DOCUMENTS

| | | | |
|---|---|---|---|
| 2012/0022665 A1 | 1/2012 | Kyomoto et al. | |
| 2013/0071930 A1* | 3/2013 | Chu | A61L 27/54 525/379 |
| 2013/0330394 A1 | 12/2013 | Ponticiello et al. | |
| 2015/0011673 A1 | 1/2015 | Yamagawa et al. | |

FOREIGN PATENT DOCUMENTS

| | | |
|---|---|---|
| JP | 62-038170 | 2/1987 |
| JP | 11-000341 | 1/1999 |
| JP | 2005-112848 | 4/2005 |
| JP | 2008-245775 | 10/2008 |
| JP | 2008-272385 | 11/2008 |
| JP | 2009-034302 | 2/2009 |
| JP | 2009-061104 | 3/2009 |
| JP | 2009-178281 | 8/2009 |
| JP | 2009-178392 | 8/2009 |
| JP | 2010-035827 | 2/2010 |
| JP | 2010-504158 | 2/2010 |
| JP | 2010-253195 | 11/2010 |
| JP | 2011-078624 | 4/2011 |
| JP | 2011-125531 | 6/2011 |
| JP | 2013-022234 | 2/2013 |
| JP | 2013-144778 | 7/2013 |
| JP | 2014-014579 | 1/2014 |
| JP | 2014-506509 | 3/2014 |
| WO | 2008/023604 | 2/2008 |
| WO | 2011/091411 A2 | 7/2011 |

OTHER PUBLICATIONS

Inagaki Masahiko, JP 2008272385, Trans. description in PE2E (Year: 2008).*
Kasahara Shinjiro et al. (JP 2011125531) (Year: 2011).*
Sailaja S Gopalakrishnanchettiyar et al., "Surface-Phosphorylated Copolymer Promotes Direct Bone Bonding", Tissue Engineering Part A, 2009, vol. 15, No. 10, May 25, 2009, pp. 3061-3069.
Michael R. Mucalo et al., "Phosphorylated, cellulose-based substrates as potential adsorbents for bone morphogenetic proteins in biomedical applications: A protein adsorption screening study using cytochrome C as a bone morphogenetic protein mimic", Colloids and Surfaces B: Biointerfaces, vol. 71, 2009, Jan. 13, 2009, pp. 52-58.
The Society of Synthetic Organic Chemistry, Japan, Organic chemistry handbook, Jul. 10, 1968, pp. 595, 601, with English language translation.
Vrushali Bhagat et al., "Caddisfly Inspired Phosphorylated Poly-(ester urea)-Based Degradable Bone Adhesives", Biomacromolecules, 2016, vol. 17, Jul. 12, 2016, pp. 3016-3024.
International Search Report in International Application No. PCT/JP2018/018837, filed Aug. 21, 2018.
International Preliminary Report on Patentability in International Application No. PCT/JP2018/018837, filed Nov. 19, 2019.
Extended European Search Report, EPO, Application No. 18802641.3, dated Jan. 22, 2021.
Self-initiated surface grafting with poly(2-methacryloyloxyethyl phosphorylcholine) on poly(ether-ether-ketone), M. Kyomoto et al, Biomaterials, Elsevier, Amsterdam, NL, issued Feb. 1, 2020, pp. 1071-1024.

* cited by examiner

[Figure 1]
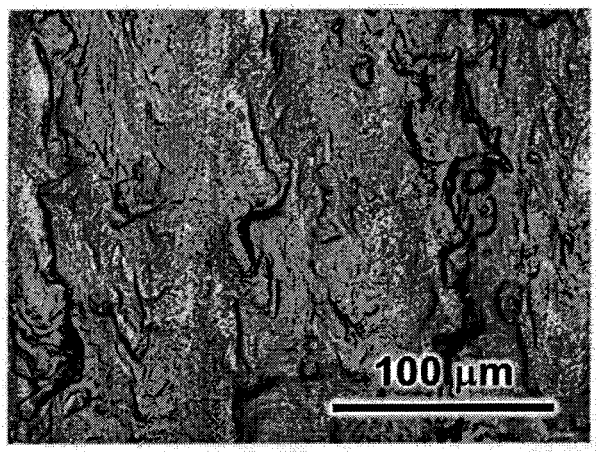
[Figure 2]
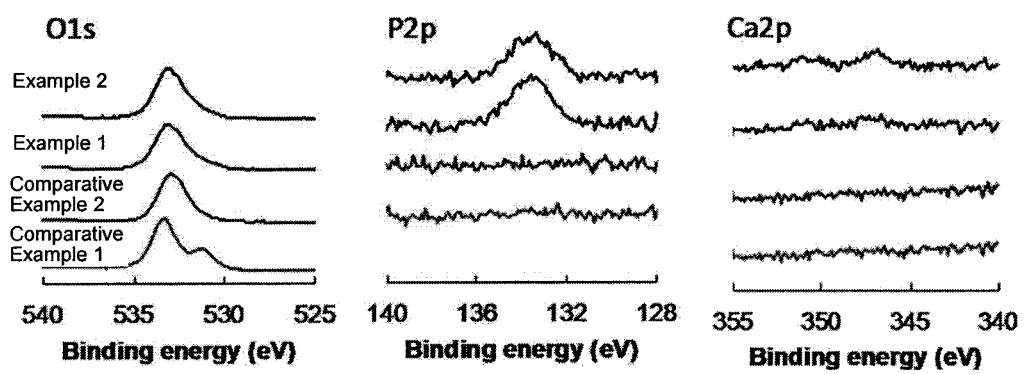
[Figure 3]
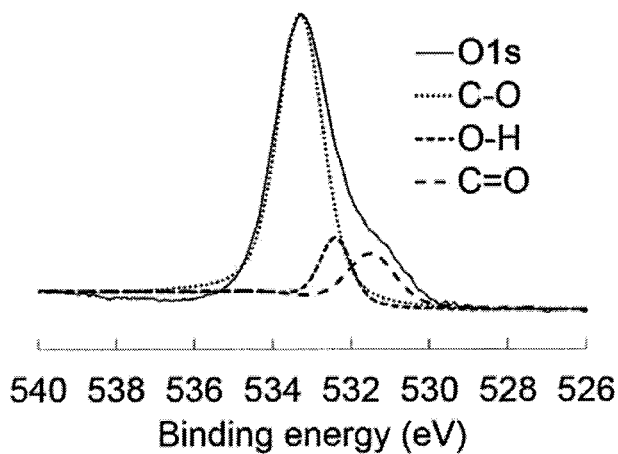

[Figure 4]
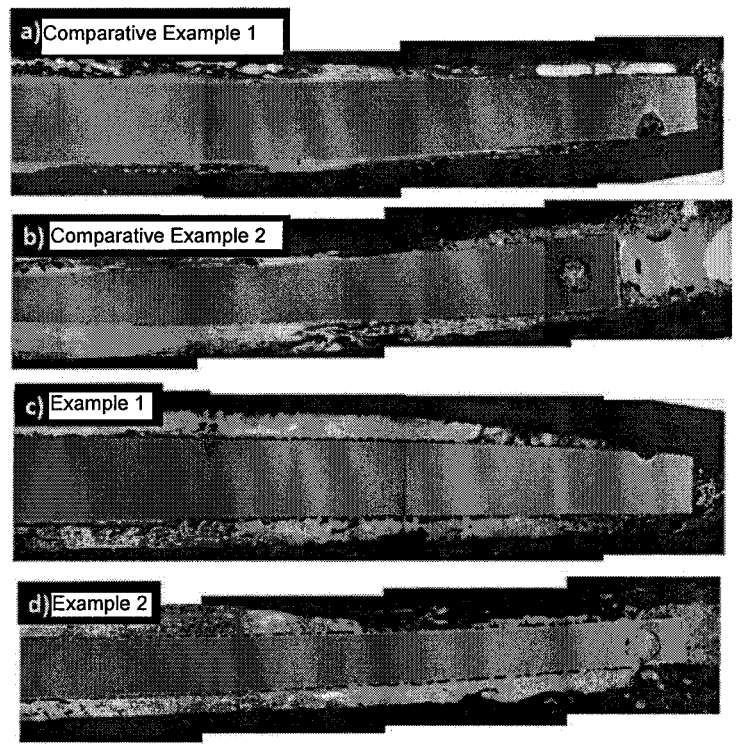
[Figure 5]
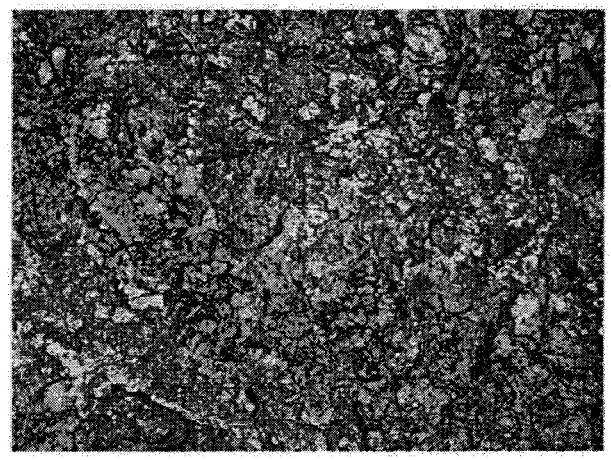

MEDICAL POLYMER MATERIAL HAVING EXCELLENT BONE-BONDING PROPERTY

TECHNICAL FIELD

The present invention relates to a medical polymer material and a method for producing the same. More specifically, the present invention relates to a polymer material for medical implants that exhibits a bone-bonding property, and a method for producing the same.

BACKGROUND ART

Among medical materials, medical implant materials are materials that are used for the prosthesis or repair of living tissue defects.

Although the medical implant materials differ in required properties depending on defective tissues or cases, it is desired that medical implant polymer materials, such as spinal cages, which are required to substitute the dynamic functions of bone functions should fully satisfy the following: 1) presenting excellent tissue compatibility; 2) presenting a bone-bonding property (a property by which the material bonds to bone when implanted in the proximity of an existing bone); 3) presenting a Young's modulus close to that of bone; 4) having excellent mechanical properties; 5) being non-allergenic; 6) being a nonmagnetic material; and 7) being not brittle.

For example, ceramic materials such as hydroxyapatite satisfy 1) presenting excellent tissue compatibility, 2) presenting a bone-bonding property, 5) being non-allergenic, and 6) being a nonmagnetic material, but do not satisfy 3) presenting a Young's modulus close to that of bone, 4) having excellent mechanical properties, and 7) being not brittle, among the required properties.

Further, metal materials such as titanium satisfy 1) presenting excellent tissue compatibility, 2) presenting a bone-bonding property, and 4) having excellent mechanical properties, and 7) being not brittle, but do not satisfy 3) presenting a Young's modulus close to that of bone, and 5) being non-allergenic. Furthermore, such low magnetic materials do not satisfy 6) being a nonmagnetic material.

Hence, research and development are underway, focusing on polymer materials as medical implant materials. For example, polyetheretherketone (PEEK), an engineering plastic, is already clinically applied to spinal cages or the like.

Although PEEK satisfies 3) presenting a Young's modulus close to that of bone, 4) having excellent mechanical properties, 5) being non-allergenic, 6) being a nonmagnetic material, and 7) being not brittle, it does not satisfy 1) presenting excellent tissue compatibility, and 2) presenting a bone-bonding property.

Hence, approaches of improving the tissue compatibility of engineering plastics or imparting a bone-bonding property are under active research and development. In general, the bone-bonding property is conceptually higher than tissue compatibility, and excellent tissue compatibility is imparted when the bone-bonding property is imparted. On the contrary, the bone-bonding property is not always imparted even when the tissue compatibility is imparted.

For example, a method of providing calcium phosphate or the like on the surface of an engineering plastic (Patent Literatures 1 to 5) has been proposed in order to impart a bone-bonding property to the engineering plastic.

However, with this method, there are problems such as an interface is formed between calcium phosphate or the like and the engineering plastic, and the bonding force of the interface is small, or the production approach is complicated.

A method of mixing calcium phosphate or the like into an engineering plastic (Patent Literatures 6 to 10) has also been proposed. Although problems such as the separation of an interface are less likely to arise because calcium phosphate or the like is mixed into the engineering plastic, this method reduces the physical properties of the engineering plastic itself.

A method of providing a surface layer that captures calcium phosphate that presents a bone-bonding property on a polymer (Patent Literature 11) is also disclosed. However, also this method cannot circumvent problems that an interface is formed between calcium phosphate or the like and the engineering plastic, and the bonding force of the interface is small.

On the other hand, a method of allowing a surface of an engineering plastic to be porous or having a concave-convex structure so that the engineering plastic bonds mechanically to bone (Patent Literatures 12 to 14) has also been proposed. Although this method is a method of mechanically fitting and fixing the engineering plastic to bone, there was a problem that the bonding to bone is time-consuming.

A method of imparting a hydrophilic functional group to an engineering plastic surface (Patent Literature 15) has further been reported. Osteoblasts which form bone need to adhere to a material. Hydrophilicity is preferred for the adhesion of the cells, and the imparting of hydrophilicity is also a necessary condition, but not a sufficient condition, for improvement in bone-bonding property.

Patent Literature 15 states that "the method for imparting the hydrophilic functional group is preferably low-pressure oxygen plasma treatment, UV ozone treatment or atmospheric-pressure plasma treatment, and atmospheric-pressure plasma treatment which can particularly produce excellent hydrophilic surfaces is particularly preferred". This disclosed approach is appropriate as an approach of introducing a hydroxy group to a polymer material. However, the production method cannot impart a phosphate or sulfate group listed as an example of a hydrophilic group other than a hydroxy group to a surface, and Examples or the like have no mention about this, as a matter of course.

For a product of Patent Literature 15, it is necessary to impart hydrophilicity of 30% or more in terms of the area ratio of a peak corresponding to the hydrophilic functional group when a peak obtained by X-ray photoelectron spectroscopic measurement is subjected to waveform separation as to the central atom of the hydrophilic functional group. The literature states that "the central atom is an atom directly bonded to the main chain of PEEK among the atoms contained in the hydrophilic functional group".

Although the disclosed approach is appropriate as an approach of introducing oxygen which is the central element of a hydroxy group to the main chain of a polymer material, phosphorus designated as the central element of a phosphate group listed as an example of a hydrophilic group other than a hydroxy group, or sulfur designated as the central element of a sulfate group, cannot be directly bonded to the main chain of PEEK with this production method. When forming a hydroxy group on a ketone group, the ratio between the ketone group and the hydroxy group is meaningful. On the other hand, this does not mean anything for the phosphate or sulfate group.

Here, in the present invention, compound names, etc. are based on International Union of Pure and Applied Chemistry (IUPAC). IUPAC defines a polymer in Gold Book, and defines the main chain as "That linear chain to which all other chains, long or short or both, may be regarded as being pendant".

Thus, in the present invention, for example, a hydroxy group formed by reducing the ketone group of PEEK is defined as a side chain bonded to carbon in the main chain. Likewise, while a hydroxy group is formed on a benzene ring by treating PEEK by ozone treatment or the like, this hydroxy group is also defined as a side chain bonded to carbon in the main chain.

Accordingly, any approach for sufficiently improving the bone-bonding property of a medical polymer material through the chemical bonding of a phosphate group has not yet been found heretofore.

CITATION LIST

Patent Literatures

Patent Literature 1: Japanese Patent Laid-Open Publication No. 2008-245775
Patent Literature 2: Japanese Patent Laid-Open Publication No. 2009-34302
Patent Literature 3: Japanese Patent Laid-Open Publication No. 2009-61104
Patent Literature 4: Japanese Patent Laid-Open Publication No. 2011-78624
Patent Literature 5: Japanese Patent Laid-Open Publication No. 2013-22234
Patent Literature 6: Japanese Patent Laid-Open Publication No. 2009-178281
Patent Literature 7: Japanese Patent Laid-Open Publication No. 2010-35827
Patent Literature 8: National Publication of International Patent Application No. 2010-504158
Patent Literature 9: Japanese Patent Laid-Open Publication No. 2013-144778
Patent Literature 10: Japanese Patent Laid-Open Publication No. 2014-506509
Patent Literature 11: Japanese Patent Laid-Open Publication No. 2005-112848
Patent Literature 12: Japanese Patent Laid-Open Publication No. 2009-128392
Patent Literature 13: Japanese Patent Laid-Open Publication No. 2010-253195
Patent Literature 14: Japanese Patent Laid-Open Publication No. 2014-14579
Patent Literature 15: Japanese Patent Laid-Open Publication No. 2011-125531

SUMMARY OF INVENTION

Technical Problem

An object of the present invention is to provide a medical polymer material having an excellent bone-bonding property, and a method for producing the same.

Solution to Problem

The present inventors have conducted diligent studies to solve the above-mentioned object and consequently completed the present invention by finding that a medical polymer material in which a phosphate group having a C—O—P chemical bond including elemental C in a main chain of a structural formula is present through chemical bonding on a surface of a polymer material substantially free of phosphate and hydroxy groups except for ends in the structural formula, such as PEEK, is a material that fully satisfies the following required properties as medical polymer materials; 1) presenting excellent tissue compatibility; 2) presenting a bone-bonding property; 3) presenting a Young's modulus close to that of bone; 4) having excellent mechanical properties; 5) being non-allergenic; 6) being a nonmagnetic material; and 7) being not brittle.

[1] A medical polymer material in which a phosphate group having a C—O—P chemical bond including elemental C in a main chain of a structural formula is present on a surface of a polymer material substantially free of phosphate and hydroxy groups except for ends in the structural formula.

[2] The medical polymer material according to [1], wherein the phosphate group having a C—O—P chemical bond including elemental C in a main chain of a structural formula, and a hydroxy group having a C—O—H chemical bond including elemental C in the main chain are both present on the surface of the polymer material.

[3] The medical polymer material according to [1] or [2], wherein calcium is further imparted to the surface of the polymer material.

[4] The medical polymer material according to any one of [1] to [3], wherein the polymer material contains a ketone group in the structural formula.

[5] The medical polymer material according to any one of [1] to [4], wherein the polymer material is a polymer material selected from polyetherketone, polyarylate, polycarbonate, polyester, and polyethylene terephthalate.

[6] The medical polymer material according to any one of [1] to [5], wherein the polymer material is polyetheretherketone.

[7] The medical polymer material according to any one of [1] to [6], wherein an arithmetic average roughness Ra of the surface of the polymer material is 1 μm or larger.

[8] The medical polymer material according to any one of [1] to [7], wherein grooves are formed on the surface of the polymer material, and the grooves have an intergroove distance of 200 μm or smaller and a groove depth of 10 μm or larger.

[9] A method for producing a medical polymer material according to any one of [1] to [8], comprising forming a hydroxy group on a starting polymer material surface substantially free of phosphate and hydroxy groups except for ends in a structural formula, and phosphorylating the whole or a portion of the hydroxy group.

[10] The method for producing a medical polymer material according to [9], wherein the starting polymer material is a polymer material having a ketone group in the structural formula, and the hydroxy group is formed on the starting polymer material surface by reducing the ketone group on the starting polymer material surface.

[11] The method for producing a medical polymer material according to [9], wherein the hydroxy group is formed on the starting polymer material surface by at least one method selected from an ozone exposure method, a plasma irradiation method, and an ultraviolet irradiation method.

[12] The method for producing a medical polymer material according to any one of [9] to [11], wherein the hydroxy group formed on the starting polymer material surface is phosphorylated using phosphoryl chloride or dialkyl chlorophosphate.

[13] The method for producing a medical polymer material according to any one of [9] to [12], further comprising imparting calcium to the phosphorylated surface of the starting polymer material.

BRIEF DESCRIPTION OF DRAWINGS

FIG. 1 is a scanning electron microscope image (SEM image) of a PEEK product produced in surface morphology formation step by grinding in Comparative Example 1.

FIG. 2 is an XPS spectrum diagram of the PEEK products produced in Comparative Examples 1 and 2 and Examples 1 and 2.

FIG. 3 is an XPS spectrum diagram of a PEEK product produced in a hydroxy group chemical bonding step by the reduction of ketone groups in Comparative Example 2.

FIG. 4 shows histopathological images 4 weeks after implantation of the PEEK products produced in Comparative Examples 1 and 2 and Examples 1 and 2.

FIG. 5 is a scanning electron microscope image (SEM image) of a PEEK product subjected to surface morphology formation treatment by sandblasting in Comparative Example 5.

DESCRIPTION OF EMBODIMENTS

A moiety, other than a surface, of the medical polymer material of the present invention consists of a polymer material substantially free of phosphate and hydroxy groups except for ends in the structural formula. The medical polymer material of the present invention employs, as a starting polymer material (a raw material polymer material), a polymer material substantially free of phosphate and hydroxy groups except for ends in the structural formula as described above. The surface of this polymer material undergoes a predetermined treatment, and the composition of a principal moiety, other than the surface, of the medical polymer material of the present invention is the starting polymer material itself.

A polymer material containing phosphate or hydroxy groups in the structural formula is not preferred because the polymer material is highly water-absorbable and does not satisfy the following required properties as medical polymer materials; 3) presenting a Young's modulus close to that of bone; and 4) having excellent mechanical properties.

While some starting polymer materials have a hydroxy group or the like at an end, even polymer materials having hydroxy or phosphate groups at the ends of the structural formulas are encompassed in the present invention because this terminal hydroxy group or the like has only limited influence on the properties of bulk polymer materials.

Likewise, hydroxy or phosphate groups contained in a very small portion of the structural formula of a starting polymer material have only limited influence on the properties of bulk polymer materials. Hence, the starting polymer material according to the present invention is required to be the polymer material substantially free of phosphate and hydroxy groups in the structural formula except for ends as described above.

The phrase "substantially free of phosphate and hydroxy groups except for ends" means that there are no phosphate and hydroxy groups excluding phosphate and hydroxy groups inevitably added in production to a moiety other than the ends, and means that, for example, the molecular weights of phosphate and hydroxy groups contained in the moiety other than the ends are less than 1%, preferably less than 0.5%, with respect to the molecular weight of the structural formula.

In the present invention, the presence of a phosphate group having a C—O—P chemical bond including elemental C in a main chain on the surface of the medical polymer material is an essential condition. The essential condition markedly improves the ability of the material to form bone. Although the mechanism underlying this marked improvement in ability to form bone has not yet been elucidated, this may be partly because a protein adsorbed to the phosphate group on the medical polymer material surface contributes to the adhesion, etc. of osteoblasts or the like.

The amount of the phosphate group is not particularly limited, and the atomic percentage of the phosphate on the medical polymer material surface is preferably 0.1% or more, more preferably 0.5% or more, further preferably 1.0% or more, in XPS measurement from the viewpoint of efficient osteoconductivities, etc.

In the present invention, the case where not only a phosphate group having a C—O—P chemical bond including elemental C in a main chain but also a hydroxy group having a C—O—H chemical bond including elemental C in the main chain is present on the surface of the medical polymer material is more preferred.

When the phosphate group and the hydroxy group coexist, the ability of the material to form bone markedly improves. Although the mechanism underlying this marked improvement in ability to form bone has not yet been elucidated, this may be partially because a protein adsorbed to the medical polymer surface contributes to the adhesion, etc. of osteoblasts or the like through the interaction between the phosphate group and the hydroxy group.

As for the amount of the hydroxy group, the atomic percentage on the medical polymer material surface in XPS measurement is preferably 0.1% or more, more preferably 0.5% or more, further preferably 1.0% or more.

In the present invention, it is preferred that calcium should be further imparted to the surface of the polymer material. Such a material has better ability to form bone.

Although the mechanism underlying the superior ability of the material to form bone has not yet been elucidated, the calcium and the phosphate group present on the surface of the polymer material interact with each other to further improve the ability to form bone because the calcium has strong affinity for phosphate and is known to contribute to the adhesion, growth, differentiation, and calcification of cells.

It suffices that the calcium is imparted to the medical polymer material, and it is basically considered to be imparted to the medical polymer material through its interaction with the phosphate group. When the medical polymer material with the phosphate group chemically bonded thereto is implanted in vivo, it is considered that calcium is imparted to the medical polymer material surface because body fluids contain calcium. Therefore, the imparting of the calcium to the medical polymer material surface is not essential. The imparting of the calcium to the medical polymer material surface beforehand is probably effective from the viewpoint of the early exertion of osteoconductivities, etc.

The amount of the calcium to be imparted is not particularly limited, and the atomic percentage of the calcium on the medical polymer material surface measured by XPS is preferably 0.1% or more, more preferably 0.5% or more, further preferably 1% or more.

The starting polymer material of the present invention preferably contains a ketone group in the structural formula. The polymer material containing ketone group is often excellent in mechanical properties. Furthermore, phosphate or, both phosphate and hydroxy groups, can be chemically bonded thereto, by reducing the ketones to form hydroxy group, followed by the whole or partial phosphorylation of the hydroxyl group.

The starting polymer material of the present invention is preferably a polymer material selected from polyetherketone, polyarylate, polycarbonate, polyester, and polyethylene terephthalate. These polymer materials are materials that contain a ketone group in their structural formulas and fully satisfy the following required property as medical polymer materials: 4) having excellent mechanical properties.

The polyetherketone in the present invention is a generic name for linear polymers formed by the bonding of ether and ketone. Among others, aromatic polyetherketone is useful, and the aromatic polyetherketone is a linear polymer formed from benzene rings bonded via ether and ketone.

Examples of such polyetherketone include polyetherketone (PEK) having a basic linear structure where ether and ketone bonds are alternately arranged, polyetheretherketone (PEEK) in which ether, ether, and ketone bonds are arranged in this order, polyetherketoneketone (PEKK), polyetheretherketoneketone (PEEKK), and polyetherketone ester.

Among the polyetherketones, particularly, PEEK is one of the polymer materials most suitable as medical polymers because PEEK is similar in dynamic properties to bone and has already been clinically applied.

These starting polymer materials are processed into a desired shape by various molding methods such as extrusion molding or injection molding. At this time, carbon fiber, calcium phosphates, or the like may be added inside the starting polymer material for the purpose of increasing mechanical strength, imparting of a bone-bonding property, etc.

If a starting polymer material without surface roughening is used, a medical polymer material having excellent ability to bond to bone, etc. can be produced by chemically bonding a phosphate group having a C—O—P chemical bond including elemental C in a main chain, to the material surface. However, when the phosphate group is chemically bonded to a roughened surface of the starting polymer material, it is extremely useful from the viewpoint of the ability to bond to bone, etc. The surface roughness (arithmetic average roughness Ra) of the starting polymer material is preferably 1 μm or larger, more preferably 1.2 μm or larger, further preferably 1.5 μm or larger, particularly preferably 1.7 μm or larger.

The formation of grooves on the surface of the starting polymer material is also very useful from the viewpoint of the ability to bond to bone. The grooves preferably have an intergroove distance of 200 μm or smaller and a groove depth of 10 μm or larger. The chemical bonding of the phosphate group to the surface of the starting polymer material having the grooves having an intergroove distance of 200 μm or smaller and a groove depth of 10 μm or larger is extremely useful from the viewpoint of the ability to bond to bone, etc. The intergroove distance is more preferably 170 μm or smaller, further preferably 140 μm or smaller, particularly preferably 110 μm or smaller. The groove depth is more preferably 15 μm or larger, further preferably 20 μm or larger, particularly preferably 25 μm or larger.

The groove depth and the intergroove distance can be measured under a 3D laser microscope or the like.

In the medical polymer material of the present invention, when the arithmetic surface roughness (Ra) of the polymer surface is 1 μm or larger and the phosphate group is chemically bonded to the surface of the polymer material, and when the polymer surface has grooves having an intergroove distance of 200 μm or smaller and a groove depth of 10 μm or larger and the phosphate group is chemically bonded to the surface of the polymer material the bone-bonding property or the like is particularly superior.

The reason why the combination of both conditions exerts excellent properties, particularly, in terms of osteoconductivities or the like, cannot be simply explained by the combined effects of both conditions, and the mechanism thereof is unknown. It may be possible that a microenvironment is formed on the surface of the medical polymer material, and the presence of phosphate groups or both phosphate and hydroxy groups in the microenvironment exerts a specific effect of conducting bone to the microenvironment.

In the present invention, a medical polymer material is produced in which a phosphate group having a C—O—P chemical bond including elemental C in a main chain of a structural formula is present on a surface of a polymer material substantially free of phosphate and hydroxy groups except for ends in the structural formula.

A method for producing the material comprises forming a hydroxy group on a starting polymer material surface substantially free of phosphate and hydroxy groups except for ends in a structural formula, and phosphorylating the whole or a portion of the hydroxy group at the same time with or subsequently to the hydroxy group formation step.

When a ketone group is present in the starting polymer material, an effective production method comprises forming a hydroxy group on the starting polymer material surface by reducing the ketone group, followed by phosphorylating the whole or a portion of the hydroxy group. The reduction of the ketone group can form a hydroxy group on the starting polymer material surface without cleaving the main chain of the starting polymer material. Thus, a medical polymer material having high quality can be produced.

Sodium borohydride ($NaBH_4$), lithium borohydride ($LiBH_4$), lithium aluminum hydride ($LiAlH_4$), monoborane ($BH_3$), or the like can be used as a reducing agent to be used in the reduction of the ketone group.

When a benzene ring is present in the starting polymer material, an effective production method comprises forming a hydroxy group on the polymer material surface by oxidizing the benzene ring, followed by phosphorylating the whole or a portion of the hydroxy group. The oxidation of the benzene ring can form a hydroxy group on the starting polymer material surface without cleaving the main chain of the starting polymer material. Thus, a medical polymer material having high quality can be produced. For the oxidation of the benzene rings, reaction with ozone is preferred from the viewpoint of efficiency. The oxidation of the benzene ring with ozone is preferably performed at a low temperature. The temperature is preferably 10° C. or lower, more preferably −20° C. or lower, further preferably −50° C. or lower.

An alternative method for producing a medical polymer material in which a phosphate group having a C—O—P chemical bond including elemental C in a main chain is chemically bonded to the surface of the starting polymer material comprises cleaving between elements of the starting polymer material by at least one method selected from an ozone exposure method, a plasma irradiation method, and an ultraviolet irradiation method, followed by reacting with moisture or the like to form a hydroxy group, followed by phosphorylating the whole or a portion of a hydroxy group.

Examples of the phosphorylation approach include an approach of exposing the starting polymer material with a hydroxy group formed on the surface to a phosphate source, and chemically bonding the phosphate group thereto via the hydroxy group through chemical reaction such as dehydration. In the case of dehydration reaction, hydrogen of the hydroxy group on the starting material surface is eliminated from the bonding so that a C—O—P chemical bond including elemental C in a main chain is formed.

Specifically, the hydroxy group on the starting polymer material surface is preferably phosphorylated with phosphoryl chloride or dialkyl chlorophosphate such as dimethyl chlorophosphate or diethyl chlorophosphate.

These compounds have a high phosphorylation ability and permit phosphorylation treatment in a predetermined amount without a high-temperature reaction. Also, the phosphorylation of the hydroxy group of the starting polymer material at a relatively high temperature can increase the amount of phosphate groups chemically bonded to the starting polymer material.

A method for producing a medical polymer material in which calcium is further imparted to the material surface having a C—O—P chemical bond comprises producing a polymer material provided with both phosphate and hydroxy groups, and contacting the material with calcium.

The medical polymer material in which calcium is imparted to the surface is produced, for example, by immersing a polymer material with a phosphate group chemically bonded to the surface in an aqueous solution containing calcium ions, such as a calcium chloride aqueous solution.

When the production method involves dipping the polymer material in an aqueous solution containing calcium as an approach of imparting calcium to the surface of the polymer material, the calcium concentration of the calcium solution is preferably 1 m mol/L or higher and 5 mol/L or lower, more preferably 10 m mol/L or higher and 3 mol/L or lower, further preferably 50 m mol/L or higher and 2 mol/L or lower, from the viewpoint of efficient imparting of calcium to the medical polymer material surface.

EXAMPLES

Hereinafter, the properties (bone-bonding property) of the medical polymer material according to the present invention and a method for producing the same will be described with reference to specific examples. In the present Examples and Comparative Examples, studies were conducted under the conditions described below.

(Surface Morphology Formation Step by Sandblasting)

A rod-shaped PEEK material having a diameter of 1.4 mm and a length of 2.3 mm was sandblasted with alumina as abrasive grains. Ra of the surface formed by this step was 2.3 μm.

(Surface Morphology Formation Step by Grinding)

A rod-shaped PEEK material having a diameter of 1.4 mm and a length of 2.3 mm was ground for the surface roughening of the material surface. Ra of the surface formed by this step was 2.3 μm. The intergroove distance was 100 μm, and the groove depth was 38.5 μm.

(Hydroxy Group Formation Step by Reduction of Ketone Group)

The ketone groups of PEEK were reduced by immersing a PEEK material in a 80° C. dimethyl sulfoxide solution of 0.05 mol/L sodium borohydride for 24 hours.

(Hydroxy Group Chemical Bonding Step by Ozone Treatment)

Ozone treatment was performed by treating a polymer material in an ozone generator for research and development manufactured by EcoDesign, Inc. at room temperature for 1 hour.

(Hydroxy Group Chemical Bonding Step by Plasma Treatment)

Plasma treatment was performed by treating a polymer material in CUTE 1MP manufactured by Femto Science Inc. at 50 kHz and 100 W for 1 minute.

(Phosphate Group Chemical Bonding Step)

A phosphate group chemical bonding step was performed by immersing a material in phosphoryl chloride.

Specifically, 0.9 mL of phosphoryl chloride was mixed with 1.4 mL of triethylamine and 100 mL of dichloromethane to prepare a phosphoryl chloride solution. The material to be treated was immersed in the 20° C. phosphoryl chloride solution for 24 hours.

(Calcium Imparting Step)

A material with phosphate groups chemically bonded to the surface was dipped in a 20° C. 0.1 mol/L calcium chloride aqueous solution for 1 hour.

(XPS Measurement)

XPS analysis of a sample was performed in K-Alpha+ system manufactured by Thermo Fisher Scientific Inc.

(Evaluation Using Cultured Cell)

A produced material was placed in a plastic culture dish, and 25,000 mesenchymal stem cells extracted from the rat femur were seeded over the materials. Cell counting kit-8 manufactured by Dojindo Laboratories was used in the evaluation of cell proliferation numbers. LabAssay™ ALP manufactured by Wako Pure Chemical Industries, Ltd. was used in the measurement of alkaline phosphatase activity. Calcification staining kit manufactured by Cosmo Bio Co., Ltd. was used in the evaluation of the amount of bone nodules formed.

(Histopathological Examination)

A bone defect having a diameter of 1.5 mm was formed in the longitudinal direction in a rat femur, and the produced material was implanted in the bone defect. The material was taken out with surrounding tissues 4 weeks after the implantation, and histopathological sections were prepared and stained with hematoxylin-eosin or by the Villanueva-Goldner method.

(Bone-Material Bonding Rate)

The length of a material contacted with bone in a histopathological image obtained by hematoxylin-eosin staining was divided by the length of the material facing the bone, and the obtained value was indicated in percentage.

(Pull-Out Strength (Shear Force Against Bone))

A defect of 1.5 mmϕ was formed in the femoral canal of a 12-week-old male Wistar rat, and a cylindrical rod-shaped material having a diameter of 1.4 mm and a length of 2.3 mm was implanted therein. Then, a pull-out test in the bone marrow direction was conducted 4 weeks later.

(Detaching Strength (Detaching Force Against Bone))

A defect of 10 mm×2 mm×15 mm was formed in the tibia bone of a 12-week-old male Wistar rat, and a plate-shaped material having a side of 10 mm was implanted therein. Then, a tensile test in a direction perpendicular to the bone marrow was conducted 4 weeks later.

Grinding Group

Comparative Example 1

(Surface Morphology Formation Step)

A PEEK material surface was subjected to surface morphology formation by grinding. The PEEK material after the surface morphology formation had a Ra of 2.3 μm, an intergroove distance of 100 μm, and a groove depth of 38.5 μm. The photograph of the produced PEEK product is shown in FIG. 1. XPS analysis results are shown in FIG. 2. Peak separation results of an XPS peak are shown in Table 1.

TABLE 1

XPS analysis results in Comparative Examples 1 and 2

| Bonding energy (eV) | Assignment | Relative area Comparative Example 1 | Comparative Example 2 |
|---|---|---|---|
| 531.3-531.7 | O═C | 32.1 ± 1.0 | 13.1 ± 1.8 |
| 532.4 | O—H | 0.0 | 11.4 ± 2.0 |
| 533.3 | O—C | 67.9 ± 1.0 | 75.5 ± 2.2 |

The present material is a PEEK material and is a polymer material substantially free of phosphate and hydroxy groups except for ends in the structural formula, because the material is not changed except for morphology. Also, the PEEK product produced in Comparative Example 1 is a material that is not encompassed in the present invention because no phosphate group is chemically bonded to the surface.

Comparative Example 2

(Hydroxy Group Chemical Bonding Step)

A PEEK material obtained in the same way as in Comparative Example 1 was immersed in a 80° C. dimethyl sulfoxide solution of 0.05 mol/L sodium borohydride for 24 hours and then immersed in 0.5 mol/L hydrochloric acid so that a portion of the ketone groups of the PEEK material was reduced into hydroxy groups.

The PEEK material after the hydroxy group chemical bonding step had a Ra of 2.3 µm, an intergroove distance of 100 µm, and a groove depth of 38.5 µm. From the comparison with Comparative Example 1, it was found that the surface morphology of the PEEK material is not changed at all even by performing a hydroxy group chemical bonding treatment to the PEEK material.

XPS analysis results of the produced PEEK product are shown in FIG. 2, and peak separation results of an XPS peak are shown in FIG. 3 and Table 1.

It was confirmed that hydroxy groups were formed on the PEEK surface. The hydroxy groups are a side chain of PEEK and are hydroxy groups having a C—O—H chemical bond including elemental C in the main chain of PEEK.

The produced PEEK material is free of surface phosphate groups and is therefore a material that is not encompassed in the present invention, though hydroxy groups are chemically bonded to the surface.

Example 1

(Phosphate Group Chemical Bonding Step)

A PEEK material obtained in the same way as in Comparative Example 2 was immersed in a 20° C. mixed solution containing 0.9 mL of phosphoryl chloride, 1.4 mL of triethylamine, and 100 mL of dichloromethane for 24 hours to phosphorylate a portion of the hydroxy groups formed by reducing a portion of the ketone groups of the PEEK material.

The PEEK material after the phosphate group chemical bonding step had a Ra of 2.3 µm, an intergroove distance of 100 µm, and a groove depth of 38.5 µm. From the comparison of Example 1 with Comparative Example 2, it was found that the surface morphology of the PEEK material is not changed at all even by performing a phosphate group chemical bonding treatment of the PEEK material.

XPS analysis results of the produced PEEK product are shown in FIG. 2. It was found that a phosphate group having a C—O—P chemical bond including elemental C in a main chain of PEEK was chemically bonded to the PEEK material surface through the reaction of the hydroxy groups on the PEEK material surface with phosphoryl chloride. The atomic percentage of the phosphate group was 1.2%.

Example 2

(Calcium Imparting Step)

A PEEK material obtained in the same way as in Example 1 was immersed in a 20° C. 0.1 mol/L calcium chloride aqueous solution for 1 hour.

The PEEK material after the calcium imparting step had a Ra of 2.3 µm, an intergroove distance of 100 µm, and a groove depth of 38.5 µm. From the comparison of Example 2 with Example 1, it was found that the surface morphology of the PEEK material with phosphate groups chemically bonded to the surface is not changed at all even by performing a calcium imparting treatment to the PEEK material.

XPS analysis results of the produced PEEK product are shown in FIG. 2. It was found that calcium was imparted to the PEEK material surface.

Comparative Example 3

(Phosphate Group Chemical Bonding Step)

PEEK obtained in the same way as in Comparative Example 1 was only subjected to the phosphate group chemical bonding treatment described in Example 1 without performing the hydroxy group bonding treatment described in Comparative Example 2.

XPS analysis revealed that no phosphate group was bonded to the PEEK surface. Thus, it was found that no phosphate group can be chemically bonded to the PEEK material surface without performing the hydroxy group chemical bonding treatment performed in Comparative Example 2.

Comparative Example 4

(Study on Phosphate Group Chemical Bonding Step by Plasma Treatment)

A PEEK material obtained in the same way as in Comparative Example 1 was irradiated with plasma at 50 kHz and 100 W for 1 minute. Alternatively, a PEEK material was irradiated with plasma in the same way as above in the presence of phosphate in a reaction vessel. In either case, no phosphate group was detected on the PEEK material surface by XPS analysis. It was found that no phosphate group can be bonded to the PEEK material surface by plasma irradiation.

Analysis of PEEK Materials Produced in Comparative Examples 1 and 2 and Examples 1 and 2

The XPS spectra of oxygen ($O_{1s}$), phosphate groups ($P_{2p}$) and calcium ($Ca_{2p}$) in the PEEK materials produced in Comparative Examples 1 and 2 and Examples 1 and 2 are shown in FIG. 2.

The PEEK material before the hydroxy group formation treatment (Comparative Example 1) and the PEEK material after the hydroxy group chemical bonding treatment (Comparative Example 2) were free of both phosphorus and calcium. As shown, on the PEEK material after the phosphate group chemical bonding treatment (Example 1), phosphorus was detected, and phosphate groups were chemically bonded, though calcium was absent. On the PEEK material obtained by the calcium imparting treatment of the PEEK material of Example 1 (Example 2), phosphorus and calcium were detected.

In order to study the detailed hydroxy group formation of the PEEK material produced in Comparative Example 2, peak separation results of $O_{1s}$ are shown in FIG. 3. When $O_{1s}$ (oxygen) in XPS was analyzed by waveform separation, oxygen assigned to ketone and ether and oxygen assigned to hydroxy groups were 89% and 11%, respectively, in terms of area ratio.

As shown, the PEEK material of Comparative Example 1 was free of hydroxy groups, whereas hydroxy groups were formed on the PEEK material of Comparative Example 2, which underwent the hydroxy group chemical bonding treatment. As also shown, the formed hydroxy groups were 11.4% with respect to O.

Among the functional groups on the PEEK material surface of Example 1, phosphate groups were 0.8%. If all the hydroxy groups of the PEEK material produced in Comparative Example 2 are converted into phosphate groups by the phosphate group chemical bonding treatment, hydroxy groups are calculated to be approximately 0.57%. Hence, it was found that hydroxy and phosphate groups were present on the PEEK material surface of Example 1. Since the number of hydroxy groups was not decreased by the calcium imparting treatment, it was found that hydroxy and phosphate groups were also present on the PEEK material surface of Example 2.

Analysis on Bonding of PEEK Materials Produced in Comparative Examples 1 and 2 and Examples 1 and 2 to Bone In order to verify the ability to form bone of each PEEK product, a bone defect having a diameter of 1.5 mm was created in the longitudinal direction in a rat femur, and the untreated PEEK material, the hydroxy group-formed PEEK material, the phosphorylated PEEK material, and the Ca-imparted PEEK material were implanted therein for 4 weeks.

FIG. 4 shows histopathological images on week 4 of the PEEK products produced in Comparative Examples 1 and 2 and Examples 1 and 2 in the rat femur.

Table 2 shows the rates of bone-material bonding and pull-out strength on week 4 after implantation of the PEEK materials.

TABLE 2

Analysis results about bonding of PEEK material to bone (week 4 after implantation)

| | Bone-bonding rate | Pull-out strength |
|---|---|---|
| Comparative Example 1 | 14.7% | 12.2N |
| Comparative Example 2 | 17.4% | 23.2N |
| Example 1 | 36.9% | 34.2N |
| Example 2 | 42.8% | 42.1N |

As shown from the histopathological images and the bone-bonding rate shown in Table 2, Examples 1 and 2 are far superior in the bone-bonding rate to Comparative Examples 1 and 2. As shown from the pull-out strength shown in Table 2, Examples 1 and 2 are superior in bone-bonding force to Comparative Examples 1 and 2.

Sandblast Group

Comparative Example 5

(Surface Morphology Formation Step)

A rod-shaped PEEK material having a diameter of 1.4 mm and a length of 2.3 mm was subjected to surface morphology formation treatment by sandblasting. The PEEK material after the surface morphology formation had a Ra of 3.6 µm. The SEM photograph of the produced PEEK product is shown in FIG. 5.

The present material is a PEEK material and is a polymer material substantially free of phosphate and hydroxy groups except for ends in the structural formula, because the material is not changed except for morphology. Also, the PEEK product produced in Comparative Example 5 is a material that is not encompassed in the present invention because no phosphate group is chemically bonded to the surface.

Comparative Example 6

(Hydroxy Group Chemical Bonding Step)

A PEEK material obtained in the same way as in Comparative Example 5 was subjected to hydroxy group chemical bonding treatment under the same conditions as in Comparative Example 2.

The PEEK material after the hydroxy group chemical bonding step had a Ra of 3.6 µm. It was found that the surface morphology of the PEEK material is not changed at all even by performing the hydroxy group chemical bonding treatment of the PEEK material. Also, XPS analysis revealed that hydroxy groups were formed on the PEEK material surface. Since the hydroxy groups were formed with a reducing agent, the hydroxy groups were formed by the reduction of the ketone of the PEEK material. The hydroxy groups are a side chain of PEEK material, and are hydroxy groups having a C—O—H chemical bond including elemental C in the main chain of PEEK material.

The produced PEEK material is free of surface phosphate groups and is therefore a material that is not encompassed in the present invention, though hydroxy groups are chemically bonded to the surface.

Example 3

(Phosphate Group Chemical Bonding Step)

A PEEK material obtained in the same way as in Comparative Example 6 was subjected to phosphate group chemical bonding treatment under the same conditions as in Example 1.

The PEEK material after the phosphate group chemical bonding step had a Ra of 3.6 µm, and it was found that the surface morphology of the PEEK material is not changed at all even by performing the phosphate group chemical bonding treatment of the PEEK material.

XPS analysis revealed that phosphate groups were chemically bonded to the PEEK material surface. Since phosphoryl chloride reacts with hydroxy groups on the PEEK material surface, it was found that a phosphate group having a C—O—P chemical bond including elemental C in a main chain was formed on the PEEK material surface.

Comparative Example 7

(Phosphate Group Chemical Bonding Step)

A PEEK material obtained in the same way as in Comparative Example 5 was subjected to only the phosphate group chemical bonding treatment without performing the hydroxy group bonding treatment.

XPS analysis revealed that no phosphate group was bonded to the PEEK material surface. Thus, it was found that no phosphate group can be chemically bonded to the PEEK material surface without performing the hydroxy group chemical bonding treatment performed in Comparative Example 6.

Comparative Example 8

(Study on Phosphate Group Chemical Bonding Step by Plasma Treatment)

A PEEK material obtained in the same way as in Comparative Example 5 was irradiated with plasma at 50 kHz and 100 W for 1 minute. Alternatively, a PEEK material was irradiated with plasma in the same way as above in the presence of phosphate in a reaction container. In either case, no phosphate group was detected on the PEEK material surface by XPS analysis. It was found that no phosphate group can be bonded to the PEEK material surface by plasma irradiation.

Analysis on Bonding of PEEK Materials Produced in Comparative Examples 5 and 6 and Example 3 to Bone The PEEK materials produced in Comparative Examples 5 and 6 and Example 3 were implanted in the rat femoral canal. The pull-out strength on week 4 after implantation and detaching strength of the materials from bone are shown in Table 3.

TABLE 3

Analysis results about bonding of PEEK material to bone

|  | Pull-out strength (week 4) | Detaching strength (week 8) |
| --- | --- | --- |
| Comparative Example 5 | 8.1N | 14N |
| Comparative Example 6 | 16N | 18N |
| Example 3 | 39N | 34N |

From the pull-out strength on week 4 after implantation and the detaching strength on week 8 after implantation shown in Table 3, it was found that the PEEK material produced in Example 3 is superior in bone-bonding force to the PEEK materials produced in Comparative Examples 5 and 6.

Smooth Surface Group

Comparative Example 9

In order to study the influence of the surface morphology formation treatment of a polymer material on the bonding strength of the polymer material to bone, a PEEK material to which no surface morphology formation treatment is performed was used. The present PEEK material had a Ra of 0.06 μm.

The present polymer material is a PEEK material and is therefore a polymer material substantially free of phosphate and hydroxy groups except for ends in the structural formula. Also, the PEEK material of Comparative Example 9 is a material that is not encompassed in the present invention because no phosphate group is chemically bonded to the surface.

Comparative Example 10

(Hydroxy Group Chemical Bonding Step)

A PEEK material obtained in the same way as in Comparative Example 9 was subjected to the same hydroxy group chemical bonding treatment as in Comparative Example 2.

The PEEK material after the hydroxy group chemical bonding step had a Ra of 0.06 μm. It was found that the surface morphology of the PEEK material is not changed at all even by performing the hydroxy group chemical bonding treatment of the PEEK material.

Hydroxy groups were formed on the PEEK material surface by the reduction of the ketone groups of the starting PEEK material. The hydroxy groups are a side chain of PEEK material and are hydroxy groups having a C—O—H chemical bond including elemental C in the main chain of PEEK material.

The produced PEEK material is free of surface phosphate groups and is therefore a material that is not encompassed in the present invention, though hydroxy groups are chemically bonded to the surface.

Example 4

(Phosphate Group Chemical Bonding Step)

A PEEK material obtained in the same way as in Comparative Example 10 was subjected to phosphate group chemical bonding treatment.

The PEEK material after the phosphate group chemical bonding step had a Ra of 0.06 μm and it was found that the surface morphology of the PEEK material is not changed at all even by performing the phosphate group chemical bonding treatment of the PEEK material.

XPS analysis revealed that phosphate groups were chemically bonded to the PEEK material surface. Since phosphoryl chloride reacts with hydroxy groups on the PEEK material surface, it was found that a phosphate group having a C—O—P chemical bond including elemental C in a main chain was formed on the PEEK material surface.

Comparative Example 11

(Phosphate Group Chemical Bonding Step)

A PEEK material obtained in the same way as in Comparative Example 9 was subjected to only the phosphate group chemical bonding treatment without performing the hydroxy group chemical bonding. XPS analysis revealed that no phosphate group was bonded to the PEEK material surface. Thus, it was found that no phosphate group can be chemically bonded to the PEEK material surface by the phosphate group chemical bonding treatment without performing the hydroxy group chemical bonding treatment.

Comparative Example 12

(Study on Phosphate Group Chemical Bonding Step by Plasma Treatment)

A PEEK material obtained in the same way as in Comparative Example 9 was irradiated with plasma at 50 kHz and 100 W for 1 minute. Also, a PEEK material was irradiated with plasma in the same way as above in the presence of phosphate in a reaction vessel. In either case, no phosphate group was detected on the PEEK material surface by XPS analysis. It was found that no phosphate group can be bonded to the PEEK material surface by plasma irradiation.

Analysis on Bonding of PEEK Materials Produced in Comparative Examples 9 and 10 and Example 4 to Bone The PEEK materials produced in Comparative Examples 9 and 10 and Example 4 were implanted in the rat femoral canal. The pull-out strength and detaching strength on week 4 after implantation and detaching strength on week 8 after implantation of the materials from bone are shown in Table 4.

TABLE 4

Analysis results on bonding of PEEK material to bone

|  | Week 4 after implantation | | Week 8 after implantation Detaching strength |
|---|---|---|---|
|  | Pull-out strength | Detaching strength |  |
| Comparative Example 9 | 1.7N | 1.9N | 3.9N |
| Comparative Example 10 | 2.2N | 2.3N | 5.2N |
| Example 4 | 5.8N | 6.1N | 13.8N |

Since the PEEK material produced in Example 4 exhibited larger pull-out force and detaching force on week 4 after implantation and larger detaching force on week 8 after implantation than those of the PEEK materials produced in Comparative Examples 9 and 10, it was found that the PEEK material with phosphate groups chemically bonded to the surface has an excellent bone-bonding property.

When the pull-out strength on week 4 after implantation are compared between the PEEK material produced in Comparative Example 1 (rough surface) and the PEEK material produced in Comparative Example 9 (smooth surface), the pull-out strength of the PEEK material produced in Comparative Example 1 is larger by 10.5 N.

The difference in detaching force on week 8 after implantation between Comparative Example 9 and Example 4 (smooth surface) is 9.9 N. On the other hand, the difference in detaching force on week 8 after implantation between Comparative Example 5 and Example 3 (rough surface) is 20 N. Thus, it was found that the bonding of phosphate groups to the material surface having a Ra of 1 μm or lager exerts synergistic effects and markedly increases the bonding force of the polymer material to bone.

<Sandblasting+Ozone Treatment>

A group was studied in which hydroxy groups were formed on a PEEK material surface by ozone treatment

Comparative Example 13

(Hydroxy Group Chemical Bonding Step)

A PEEK material obtained in the same way as in Comparative Example 5 was subjected to hydroxy group chemical bonding treatment by ozone treatment. Hydroxy groups were formed on the PEEK material surface by the reduction of the ketone groups of the PEEK material. The hydroxy groups are a side chain of PEEK material and are hydroxy groups having a C—O—H chemical bond including elemental C in the main chain of PEEK material.

Ra was 3.6 μm. It was found that the surface morphology of the PEEK material is not changed at all even by performing the hydroxy group chemical bonding treatment of the PEEK material by ozone treatment.

The produced PEEK material is free of surface phosphate groups and is therefore a material that is not encompassed in the present invention, though hydroxy groups are chemically bonded to the surface.

Example 5

(Phosphate Group Chemical Bonding Step)

A PEEK material obtained in the same way as in Comparative Example 13 was subjected to phosphate group chemical bonding treatment under the same conditions as in Example 1.

The PEEK material after the phosphate group chemical bonding step had a Ra of 3.6 μm, and it was found that the surface morphology of the PEEK material is not changed at all even by performing the phosphate group chemical bonding treatment of the PEEK material.

XPS analysis revealed that phosphate groups were chemically bonded to the PEEK material surface. Since phosphoryl chloride reacts with hydroxy groups on the PEEK material surface, it was found that a phosphate group having a C—O—P chemical bond including elemental C in a main chain was formed on the PEEK material surface.

Example 6

(Calcium Imparting Step)

A PEEK material obtained in the same way as in Example 5 was immersed in a 20° C. 0.1 mol/L calcium chloride aqueous solution for 1 hour for calcium imparting treatment.

The PEEK material after the calcium imparting step had a Ra of 3.6 μm. It was found that the surface morphology of the PEEK material is not changed at all even by performing the calcium imparting treatment.

Analysis on Bonding of PEEK Materials Produced in Comparative Example 13 and Examples 5 and 6 to Bone The rates of bone-material bonding and pull-out strength on weeks 2 and 4 after implantation of the PEEK materials are shown in Table 5.

TABLE 5

Analysis results on bonding of PEEK material to bone

|  | Week 2 after implantation | | Week 4 after implantation | |
|---|---|---|---|---|
|  | Bone-bonding rate | Pull-out strength | Bone-bonding rate | Pull-out strength |
| Comparative Example 13 | 3.6% | 6.6N | 5% | 22N |

TABLE 5-continued

Analysis results on bonding of PEEK material to bone

|  | Week 2 after implantation | | Week 4 after implantation | |
| --- | --- | --- | --- | --- |
|  | Bone-bonding rate | Pull-out strength | Bone-bonding rate | Pull-out strength |
| Example 5 | 5.2% | 10N | 26% | 35N |
| Example 6 | 18% | 19N | 30% | 39N |

Since the PEEK materials produced in Examples 5 and 6 exhibited a larger bone-bonding rate and pull-out force on week 2 after implantation and a larger of bone-bonding rate and pull-out strength on week 4 after implantation than those of Comparative Example 13, it was found that the PEEK material with phosphate groups chemically bonded to the surface has an excellent bone-bonding property.

<Sandblasting+Plasma Treatment>

A group was studied in which hydroxy groups were formed by plasma treatment on the surface of a PEEK material surface-roughened by sandblasting.

Comparative Example 14

(Hydroxy Group Chemical Bonding Step)

A PEEK material obtained in the same way as in Comparative Example 5 was irradiated with plasma at 50 kHz and 100 W for 1 minute. It was confirmed by XPS that hydroxy groups were formed on the PEEK material surface. The hydroxy groups are a main chain or a side chain of PEEK and are hydroxy groups having a C—O—H chemical bond including elemental C in the main chain of PEEK.

Ra was 3.6 μm. It was found that the surface morphology of the PEEK material is not changed at all even by performing the hydroxy group chemical bonding treatment of the PEEK material with plasma.

The produced PEEK material is free of surface phosphate groups and is therefore a material that is not encompassed in the present invention, though hydroxy groups are chemically bonded to the surface.

Example 7

(Phosphate Group Chemical Bonding Step)

A PEEK material obtained in the same way as in Comparative Example 14 was subjected to phosphate group chemical bonding treatment under the same conditions as in Example 1.

The PEEK material after the phosphate group chemical bonding step had a Ra of 3.6 μm and it was found that the surface morphology of the PEEK material is not changed at all even by performing the phosphate group chemical bonding treatment of the PEEK material.

XPS analysis revealed that phosphate groups were chemically bonded to the PEEK material surface. Since phosphoryl chloride reacts with hydroxy groups on the PEEK material surface, it was found that a phosphate group having a C—O—P chemical bond including elemental C in a main chain was formed on the PEEK material surface.

Analysis on Bonding of PEEK Materials Produced in Comparative Examples 5 and 14 and Example 7 to Bone Cell proliferation rates for 7 days on the PEEK material surfaces, alkaline phosphatase activity after 14 days, and the amount of bone nodules after 21 days, and the pull-out strength of the materials from bone on week 4 after implantation are shown in Table 6.

TABLE 6

Analysis results on bonding of PEEK material to bone

|  | Cell proliferation on day 7 | ALP activity on day 14 | Bone nodule formation on day 21 | Pull-out strength on week 4 |
| --- | --- | --- | --- | --- |
| Comparative Example 5 | 100 | 100 | 100 | 8.1N |
| Comparative Example 14 | 52 | 77 | 161 | 10.2N |
| Example 7 | 252 | 194 | 223 | 14.7N |

Since the PEEK material produced in Example 7 exhibited a larger cell proliferation rate at day 7 after culture, a larger ALP activity at day 14 after culture and a larger amount of bone nodules at day 21 days after culture as compared with those of Comparative Examples 5 and 14, it was found that the PEEK material with phosphate groups chemically bonded to the surface enhances cell growth and cell differentiation involved in bone, and bone nodule formation.

<Ozone Treatment (PET Material)>

A study was conducted by forming hydroxy groups on a polyethylene terephthalate (PET) material surface by ozone treatment, and chemically bonding phosphate groups via the hydroxy groups. Ra of the starting PET material was 0.5 μm.

Comparative Example 15

A PET material was subjected to neither hydroxy group chemical bonding treatment nor phosphate group chemical bonding treatment. The PET material is a polymer material substantially free of phosphate and hydroxy groups except for ends in the structural formula, but is a material that is not encompassed in the present invention because no phosphate group is chemically bonded to the surface.

Comparative Example 16

(Hydroxy Group Chemical Bonding Step)

The PET material of Comparative Example 15 was subjected to hydroxy group chemical bonding treatment by plasma irradiation at 50 kHz and 100 W for 1 minute. The hydroxy groups are a side chain of PET material and are hydroxy groups having a C—O—H chemical bond including elemental C in the main chain of PET material.

Ra was 0.5 μm. It was found that the surface morphology of the PET material is not changed at all even by performing the hydroxy group chemical bonding treatment of the PET material.

The produced PET material is free of surface phosphate groups and is therefore a material that is not encompassed in the present invention, though hydroxy groups are chemically bonded to the surface.

Example 8

(Phosphate Group Chemical Bonding Step)

A PET material obtained in the same way as in Comparative Example 16 was subjected to phosphate group chemical bonding treatment under the same conditions as in Example 1.

The PET material after the phosphate group chemical bonding step had a Ra of 0.5 μm and it was found that the surface morphology of the PET material is not changed at all even by performing the phosphate group chemical bonding treatment of the PET material.

XPS analysis revealed that phosphate groups were chemically bonded to the PET material surface. Since phosphoryl chloride reacts with hydroxy groups on the PET material surface, it was found that a phosphate group having a C—O—P chemical bond including elemental C in a main chain was formed on the PET material surface.

Analysis on Bonding of PET Materials Produced in Comparative Example 16 and Example 8 to Bone The pull-out strength of the materials from bone on week 2 after implantation is shown in Table 7.

TABLE 7

Analysis results on bonding of PET material to bone (week 2 after implantation)

| | Pull-out strength |
|---|---|
| Comparative Example 16 | 5.8 ± 2.4N |
| Example 8 | 12 ± 3.5N |

Since the PET material produced in Example 8 exhibited a larger pull-out force on week 2 after implantation as compared with that of Comparative Example 16, it was found that the PET material with phosphate groups chemically bonded to the surface has an excellent bone-bonding property.

The invention claimed is:

1. A medical polymer material in which a phosphate group having a C—O—P chemical bond including elemental C in a main chain of a structural formula and a hydroxy group having a C—O—H chemical bond including elemental C in the main chain are both present on a surface of a polymer material substantially free of phosphate and hydroxy groups except for ends in the structural formula, wherein the polymer material contains a ketone group in the structural formula, and is selected from polyetherketone, polyarylate, polycarbonate, and polyethylene terephthalate.

2. The medical polymer material according to claim 1, wherein calcium is further imparted to the surface of the polymer material.

3. The medical polymer material according to claim 1, wherein the polymer material is polyetheretherketone.

4. The medical polymer material according to claim 1, wherein an arithmetic average roughness Ra of the surface of the polymer material is 1 μm or larger.

5. The medical polymer material according to claim 1, wherein grooves are formed on the surface of the polymer material, and the grooves have an intergroove distance of 200 μm or smaller and a groove depth of 10 μm or larger.

6. A method for producing a medical polymer material according to claim 1, comprising
forming a hydroxy group on a starting polymer material surface substantially free of phosphate and hydroxy groups except for ends in a structural formula, and phosphorylating a portion of the hydroxy group, wherein the starting polymer material contains a ketone group in the structural formula, and is selected from polyetherketone, polyarylate, polycarbonate, and polyethylene terephthalate.

7. The method for producing a medical polymer material according to claim 6, wherein the hydroxy group is formed on the starting polymer material surface by reducing the ketone group on the starting polymer material surface.

8. The method for producing a medical polymer material according to claim 6, wherein the hydroxy group is formed on the starting polymer material surface by at least one method selected from an ozone exposure method, a plasma irradiation method, and an ultraviolet irradiation method.

9. The method for producing a medical polymer material according to claim 6, wherein the hydroxy group formed on the starting polymer material surface is phosphorylated using phosphoryl chloride or dialkyl chlorophosphate.

10. The method for producing a medical polymer material according to claim 6, further comprising imparting calcium to the phosphorylated surface of the starting polymer material.

* * * * *